United States Patent
Tamaki et al.

(10) Patent No.: US 11,065,427 B2
(45) Date of Patent: Jul. 20, 2021

(54) METHOD FOR MANUFACTURING TRANSDERMAL ABSORPTION SHEET

(71) Applicant: FUJIFILM Corporation, Tokyo (JP)

(72) Inventors: Kenichiro Tamaki, Kanagawa (JP); Satoshi Wakamatsu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/005,328

(22) Filed: Aug. 28, 2020

(65) Prior Publication Data
US 2020/0391017 A1 Dec. 17, 2020

Related U.S. Application Data

(63) Continuation of application No. PCT/JP2019/003441, filed on Jan. 31, 2019.

(30) Foreign Application Priority Data

Mar. 7, 2018 (JP) .............................. JP2018-041122

(51) Int. Cl.
*A61K 45/06* (2006.01)
*A61M 37/00* (2006.01)
(Continued)

(52) U.S. Cl.
CPC ............. *A61M 37/00* (2013.01); *A61K 45/06* (2013.01); *B29C 39/003* (2013.01);
(Continued)

(58) Field of Classification Search
CPC .......... A61K 45/06; A61M 2037/0023; A61M 2207/10; A61M 37/00; B29C 39/003;
(Continued)

(56) References Cited

U.S. PATENT DOCUMENTS

| | | |
|---|---|---|
| 2008/0173563 A1 | 7/2008 | Perot |
| 2016/0045720 A1 | 2/2016 | Suzuki et al. |
| 2017/0217656 A1 | 8/2017 | Yamada |

FOREIGN PATENT DOCUMENTS

| | | |
|---|---|---|
| JP | 2004337192 | 12/2004 |
| JP | 2005249671 | 9/2005 |

(Continued)

OTHER PUBLICATIONS

"International Search Report (Form PCT/ISA/210) of PCT/JP2019/003441," dated Apr. 2, 2019, with English translation thereof, pp. 1-4.

(Continued)

*Primary Examiner* — Ernst V Arnold
(74) *Attorney, Agent, or Firm* — JCIPRNET

(57) ABSTRACT

Provided is a method for manufacturing a transdermal absorption sheet which suppresses the cost of manufacturing equipment and prevents deterioration of a pharmaceutical preparation or a raw material thereof, and an intermediate. A mold filled with a first polymer solution is stored in a drying container in an aseptic environment, and the first polymer solution in the mold stored in the drying container is dried outside an aseptic environment. In a case where a surface of the drying container in which the mold is stored is irradiated with an electron beam from an electron beam source, a shield that shields an electron beam is arranged at a position on a straight line connecting the electron beam source and the needle-like recessed portions.

14 Claims, 10 Drawing Sheets

(51) Int. Cl.
    *B29C 39/00*     (2006.01)
    *B29C 39/02*     (2006.01)
    *B29C 71/04*     (2006.01)
    B29K 105/00     (2006.01)
    B29L 31/00     (2006.01)

(52) U.S. Cl.
CPC ............ *B29C 39/026* (2013.01); *B29C 71/04* (2013.01); *A61M 2037/0023* (2013.01); *A61M 2207/10* (2013.01); *B29K 2105/0035* (2013.01); *B29L 2031/7544* (2013.01)

(58) Field of Classification Search
CPC ................. B29C 39/026; B29C 71/04; B29K 2105/0035; B29L 2031/7544
See application file for complete search history.

(56) References Cited

FOREIGN PATENT DOCUMENTS

| | | |
|---|---|---|
| JP | 2010094414 | 4/2010 |
| JP | 2010515634 | 5/2010 |
| JP | 2010233674 | 10/2010 |
| JP | 2011206178 | 10/2011 |
| JP | 2016067618 | 5/2016 |

OTHER PUBLICATIONS

"Written Opinion of the International Searching Authority (Form PCT/ISA/237) of PCT/JP2019/003441," dated Apr. 2, 2019, with English translation thereof, pp. 1-6.

METHOD FOR MANUFACTURING TRANSDERMAL ABSORPTION SHEET

CROSS-REFERENCE TO RELATED APPLICATIONS

The present application is a Continuation of PCT International Application No. PCT/JP2019/003441 filed on Jan. 31, 2019 claiming priority under 35 U.S.C § 119(a) to Japanese Patent Application No. 2018-041122 filed on Mar. 7, 2018. Each of the above applications is hereby expressly incorporated by reference, in its entirety, into the present application.

BACKGROUND OF THE INVENTION

1. Field of the Invention

The present invention relates to a method for manufacturing a transdermal absorption sheet, and particularly to a method for manufacturing a transdermal absorption sheet by shape transfer using a mold in which needle-like recessed portions are formed.

2. Description of the Related Art

A transdermal absorption sheet on which needle-like protruding portions having a high aspect ratio and containing a drug are formed is known. By attaching a transdermal absorption sheet to the surface of a living body such as skin, the drug in the needle-like protruding portions can be administered into the living body.

A transdermal absorption sheet can be manufactured by after filling needle-like recessed portions of a mold on which the needle-like recessed portions, which are inverted shapes of needle-like protruding portions, are formed with a solution containing a drug and drying a solvent, further filling the needle-like recessed portions of the mold with a solution of an excipient, drying a solvent, and peeling off the sheet from the mold (refer to JP2010-233674A and JP2011-206178A).

SUMMARY OF THE INVENTION

Since a transdermal absorption sheet is a pharmaceutical product, it is required to manufacture the transdermal absorption sheet for a step of filling a solution containing a drug into needle-like recessed portions of a mold in an aseptic environment using equipment such as an aseptic room is required. However, in a case where all steps in the manufacturing of the transdermal absorption sheet are performed in an aseptic environment, it is necessary to widen the equipment in the aseptic environment, and thus there is a problem that the equipment cost and manufacturing cost may increase.

On the other hand, it is considered that, in order to suppress the manufacturing cost, a step of sealing the mold filled with the solution in a drying container and drying the solvent of the solution outside an aseptic environment is performed. However, in a case of carrying the drying container again into an aseptic environment after drying, it is necessary to sterilize the surface of the drying container before carrying the drying container again. Here, in a case where sterilization is performed using an electron beam, there is a problem that the pharmaceutical preparation inside the needle-like recessed portions contained in the solution or the raw material thereof, and the intermediate may be deteriorated.

The present invention has been made in consideration of such circumstances, and an object thereof is to provide a method for manufacturing a transdermal absorption sheet that suppresses the cost of manufacturing equipment and prevents deterioration of a pharmaceutical preparation or a raw material thereof, and an intermediate.

In order to achieve the above object, a method for manufacturing a transdermal absorption sheet according to an aspect is a method for manufacturing a transdermal absorption sheet comprising: a first filling step of filling needle-like recessed portions of a mold having the needle-like recessed portions with a first polymer solution containing a drug in an aseptic environment; a storage step of storing the mold filled with the first polymer solution in a drying container in an aseptic environment; a carrying-out step of carrying the drying container in which the mold is stored out of the aseptic environment; a drying step of drying the first polymer solution of the mold stored in the drying container outside an aseptic environment; an electron beam irradiation step of irradiating a surface of the drying container in which the mold is stored with an electron beam from an electron beam source; and a carrying-in step of carrying the drying container into an aseptic environment after the electron beam irradiation step, in which in the electron beam irradiation step, a shield that shields an electron beam is arranged at a position on a straight line that connects the electron beam source and the needle-like recessed portions.

According to the aspect, it is possible to suppress the cost of manufacturing equipment by performing the drying step outside an aseptic environment, and to prevent deterioration of a pharmaceutical preparation or a raw material thereof, and intermediate thereof by the electron beam.

It is preferable that the shield is a drying container. Thus, it is possible to appropriately prevent deterioration of a pharmaceutical preparation and the like.

It is preferable that the drying container includes an electron beam shielding portion that shields an electron beam, and a gas permeation portion that has microbial impermeability and gas permeability and has a relatively lower electron beam shielding rate than the electron beam shielding portion, and the shield is arranged at a position on a straight line connecting the gas permeation portion and the needle-like recessed portions. Thus, it is possible to appropriately dry the first polymer solution and to appropriately prevent deterioration of a pharmaceutical preparation or the like by shielding the electron beam.

It is preferable that the electron beam shielding portion is formed of a resin or a metal. Thus, it is possible to shield the electron beam and to appropriately prevent deterioration of a pharmaceutical preparation or the like.

It is preferable that the gas permeation portion is preferably constituted of a porous sheet. Thus, it is possible to appropriately dry the first polymer solution.

It is preferable that the shield is constituted of a porous sheet. Thus, it is possible to appropriately dry the first polymer solution and to appropriately prevent deterioration of a pharmaceutical preparation or the like by shielding the electron beam.

It is preferable that the gas permeation portion is arranged on an upper surface of the drying container, and the shield is placed between the gas permeation portion and the mold. Thus, it is possible to appropriately dry the first polymer solution and to appropriately prevent deterioration of a pharmaceutical preparation or the like by shielding the electron beam.

It is preferable that the method for manufacturing a transdermal absorption sheet further comprises a cover step of covering the needle-like recessed portions of the mold filled with the first polymer solution with a holding device before the storage step, and the shield is the holding device. Thus, it is possible to appropriately prevent deterioration of a pharmaceutical preparation or the like by shielding the electron beam.

It is preferable that the holding device has a communication passage that allows an inside and an outside of the holding device to communicate with each other, and the communication passage is arranged not parallel to a straight line connecting the electron beam source and the needle-like recessed portions. Thus, it is possible to appropriately dry the first polymer solution.

It is preferable that the holding device is formed of a resin or a metal. Thus, it is possible to appropriately prevent deterioration of a pharmaceutical preparation or the like by shielding the electron beam.

It is preferable that in the electron beam irradiation step, an electron dose applied to the surface of the drying container is 15 kilo grays or more. Thus, it is possible to appropriately sterilize the surface of the drying container.

It is preferable that in the electron beam irradiation step, an electron dose applied to the needle-like recessed portions is 1 mGy or less. Thus, it is possible to appropriately prevent deterioration of a pharmaceutical preparation and the like.

It is preferable that the method for manufacturing a transdermal absorption sheet further comprises a second filling step of filling the needle-like recessed portions of the mold with a second polymer solution in an aseptic environment after the carrying-in step. Thus, it is possible to appropriately manufacture a transdermal absorption sheet.

It is preferable that the drug is peptide, protein, nucleic acid, polysaccharide, a vaccine, a medical compound belonging to a water soluble low-molecular-weight compound, or a cosmetic component. Thus, it is possible to manufacture a transdermal absorption sheet for medical use or cosmetics.

According to this invention, it is possible to suppress the cost of manufacturing equipment and to prevent deterioration of a pharmaceutical preparation or a raw material thereof, and an intermediate.

DESCRIPTION OF THE PREFERRED EMBODIMENTS

Hereinafter, preferred embodiments of the present invention will be described in detail with reference to the accompanying drawings. In the specification, "to" is used to mean that the numerical values described before and after "to" are included as a lower limit value and an upper limit value.

[Method for Manufacturing Transdermal Absorption Sheet]

Figure 1:
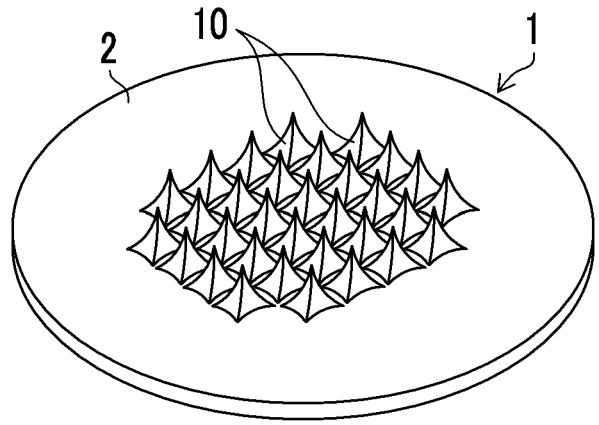
FIG. 1 is an overall perspective view of a transdermal absorption sheet.

FIG. 1 is an overall perspective view of a transdermal absorption sheet 1. As shown in FIG. 1, the transdermal absorption sheet 1 includes a sheet portion 2 and a plurality of needle-like protruding portions 10 (also called fine needles or microneedles) arranged on a surface of the sheet portion 2. Hereinafter, a method for manufacturing the transdermal absorption sheet 1 will be described.

(Production of Mold)

Figure 2:
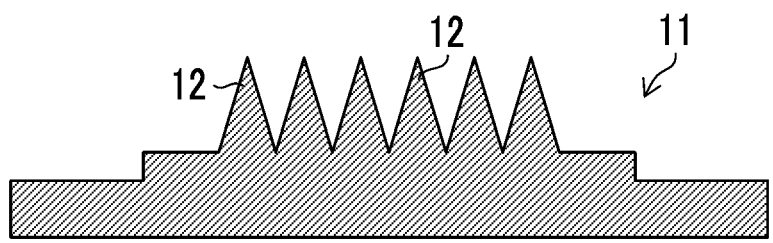
FIG. 2 is a step diagram of a method for manufacturing a mold.
Figure 3:
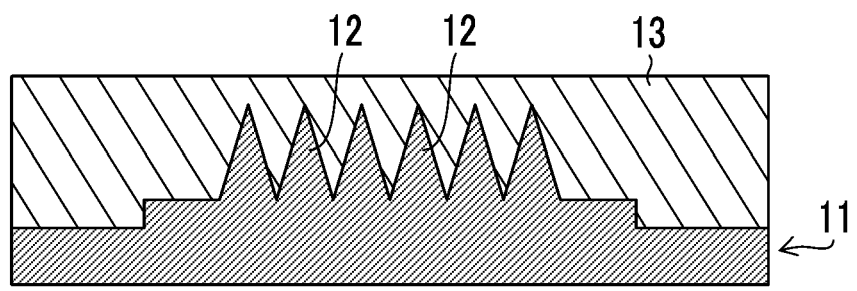
FIG. 3 is a step diagram of the method for manufacturing the mold.
Figure 4:
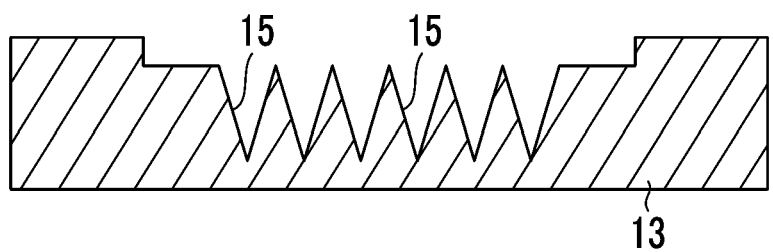
FIG. 4 is a step diagram of the method for manufacturing the mold.

FIGS. 2 to 4 are diagrams showing steps of producing a mold (die) for manufacturing a transdermal absorption sheet. As shown in FIG. 2, first, an original plate 11 for producing a mold is produced.

There are two kinds of methods for producing the original plate 11. One is a method of applying a photo resist onto a silicon substrate, then exposing and developing the photo resist, and then performing etching such as reactive ion etching (RIE) to form an array of conical shape portions (needle-like protruding portions) 12 on the surface of the original plate 11. In a case of performing etching such as RIE, the conical shape portions 12 can be formed by performing the etching in an oblique direction while the silicon substrate is being rotated.

The other is a method of machining a metal substrate of nickel or the like using a cutting tool such as a diamond byte to form an array of the shape portions 12 shaped like quadrangular pyramids or the like on the surface of the original plate 11.

Next, a mold is produced. Specifically, as shown in FIG. 3, a mold 13 is produced from the original plate 11. The following methods are conceived which enables to precisely transfer the shape of the original plate 11 to the mold 13 and then to peel off the mold 13 from the original plate 11, while manufacturing the mold at low cost.

A first method is a method of pouring, into the original plate 11, a silicone resin containing polydimethylcyloxane (for example, SYLGARD 184, manufactured by Dow Corning Toray Co., Ltd.) with a curing agent added thereto, heating and curing the silicone resin at 100° C., and then peeling off the silicon resin from the original plate 11.

A second method is a method of pouring, into the original plate 11, an ultraviolet (UV) curable resin that is curable by irradiation of ultraviolet light, irradiating the UV curable resin with ultraviolet light in a nitrogen atmosphere, and then peeling off the UV curable resin from the original plate 11.

A third method is a method of pouring a solution of a plastic resin such as polystyrene or polymethylmetacrylate dissolved into an organic solvent, into the original plate 11 coated with a release agent, volatilizing the organic solvent by drying to cure the plastic resin, and then peeling off the plastic resin from the original plate 11.

As a result, the mold 13 in which needle-like recessed portions 15 that are inverted shapes of cones or pyramids on the original plate 11 are arranged in a two-dimensional array is produced. The mold 13 produced as described above is shown in FIG. 4. The mold 13 can be easily produced any number of times using any of the above-described methods.

As a material used for the mold 13, an elastic material or a metal material can be used. Among these, a material having elasticity is preferable, and a material having high gas permeability is more preferable. Oxygen permeability, which is representative of gas permeability, is preferably more than $1\times10^{-12}$ mL/(s·m·Pa), and more preferably more than $1\times10^{-10}$ mL/(s·m·Pa). Setting the gas permeability to within the above-described range allows the air present in the needle-like recessed portions 15 of the mold 13 to be driven out from the mold side, allowing manufacturing of a transdermal absorption sheet for medial use with few defects.

Specific examples of such a material include materials obtained by melting a silicone resin (for example, SYLGARD 184 and 1310ST), a UV curable resin, or a plastic resin (for example, polystyrene or polymethylmethacrylate), and materials obtained by dissolving any of above resins into a solvent. Among these materials, silicone rubber-based materials can be suitably used due to the durability thereof against transfers using repeated pressurization and the good peelability thereof from the raw material. In addition, examples of the metal material include Ni, Cu, Cr, Mo, W, Ir, Tr, Fe, Co, MgO, Ti, Zr, Hf, V, Nb, Ta, α-aluminum oxide, zirconium oxide, and stainless steel (STAVAX), and alloys thereof.

(Polymer Solution)

The polymer solution that is a solution of the polymer resin to be used as a material of the transdermal absorption sheet 1 will be described. There are two kinds of polymer solutions. One is a solution containing a drug in a liquid (corresponding to a first polymer solution), and the other is a base liquid which mainly becomes a material for the sheet portion 2 of the transdermal absorption sheet and does not contain a drug (corresponding to a second polymer solution).

It is preferable to use a biocompatible resin as the material of the resin polymer used for the polymer solution. As such a resin, it is preferable to use sugars such as glucose, maltose, pullulan, dextran, sodium chondroitin sulfate, sodium hyaluronate, hydroxypropyl cellulose, and hydroxyethyl starch, proteins such as gelatin, or biodegradable polymers such as polylactic acid and a lactic acid-glycollic acid copolymer. Among these, sodium chondroitin sulfate, hydroxypropyl cellulose, or dextran can be preferably used. In addition, since a gelatin-based material has adhesiveness with many base materials and has a high gel strength as a material to be gelated, in a peeling-off step described later, the material can be brought into close contact with the base material to allow the polymer sheet to be peeled off from the mold using the base material. Although the concentration varies depending on the material, it is preferable that the concentration of the resin polymer in the solution is 10% to 50% by mass. In addition, the solvent used for dissolution may be other than hot water as long as the solvent has volatility, and methylethylketone, alcohol, or the like may be used. Then, a drug to be supplied into a human body can be dissolved together in the solution of the polymer resin depending on the application.

As the method for preparing the polymer solution, in a case where a water soluble polymer (gelatin or the like) is used, the solution can be produced by dissolving a water soluble powder into water, and after the dissolution, adding a chemical to the solution. In a case where the material is difficult to dissolve in water, the material may be dissolved by heating. The temperature can be appropriately selected depending on the kind of the polymer material, but the material is preferably heated at a temperature of about 60° C. or lower. In addition, in a case where a thermally melted polymer (maltose or the like) is used, the solution can be produced by dissolving the raw material and the chemical on heating. The heating temperature is preferably a temperature at which the raw material is melted, and specifically, the temperature is about 150° C.

The viscosity of the solution of the polymer resin is preferably 2000 Pa·s or less, and more preferably 1000 Pa·s or less. By appropriately adjusting the viscosity of the solution of the polymer resin, the solution can be easily injected into the recessed portions of the mold. Further, the viscosity of the liquid containing the drug is preferably 100 Pa·s or less, and more preferably 10 Pa·s or less.

(Drug)

The drug is not limited as long as the drug has the functions of a drug. Particularly, the drug is preferably selected from the group consisting of peptide, protein, nucleic acid, polysaccharide, a vaccine, a medical compound belonging to a water soluble low-molecular-weight compound, and a cosmetic component. As the water soluble polymer substance to be contained in the polymer solution containing the drug, it is preferable to use a substance which does not interact with the contained drug. For example, in a case where a protein is used as a drug, and a chargeable polymer substance is mixed with the protein, the protein and the polymer substance electrostatically interact with each other to form an associate, which is aggregated and precipitated. Therefore, in a case where a chargeable substance is used in the drug, a water soluble polymer substance with no charge such as hydroxyethyl starch or dextran is preferably used.

[Manufacturing of Transdermal Absorption Sheet]

A method for manufacturing a transdermal absorption sheet using the mold 13 will be described. The aseptic environment in the specification refers to "a manufacturing area that is classified as Grade A in the environmental monitoring method for an aseptic pharmaceutical manufacturing area, specifically, an area in which the cleanliness of air during non-working time or working time is such that the concentration of particles of 0.5 µm or more is 3520 particles/m$^3$ or less, and the concentration of particles of 5.0 µm or more is 20 particles/m$^3$ or less, and the acceptance standards for environmental microorganisms during working time are such that the concentration of floating bacteria of airborne microorganisms is 1 colony forming unit (CFU) or less/m$^3$, the concentration of falling bacteria is 1 CFU or less/plate, and the concentrations of surface adhering microorganisms are 1 CFU or less/24 to 30 cm$^2$ on a contact plate and 1 CFU or less/five fingers of a glove".

Hereinafter, each embodiment will be described.

First Embodiment

Figure 5:
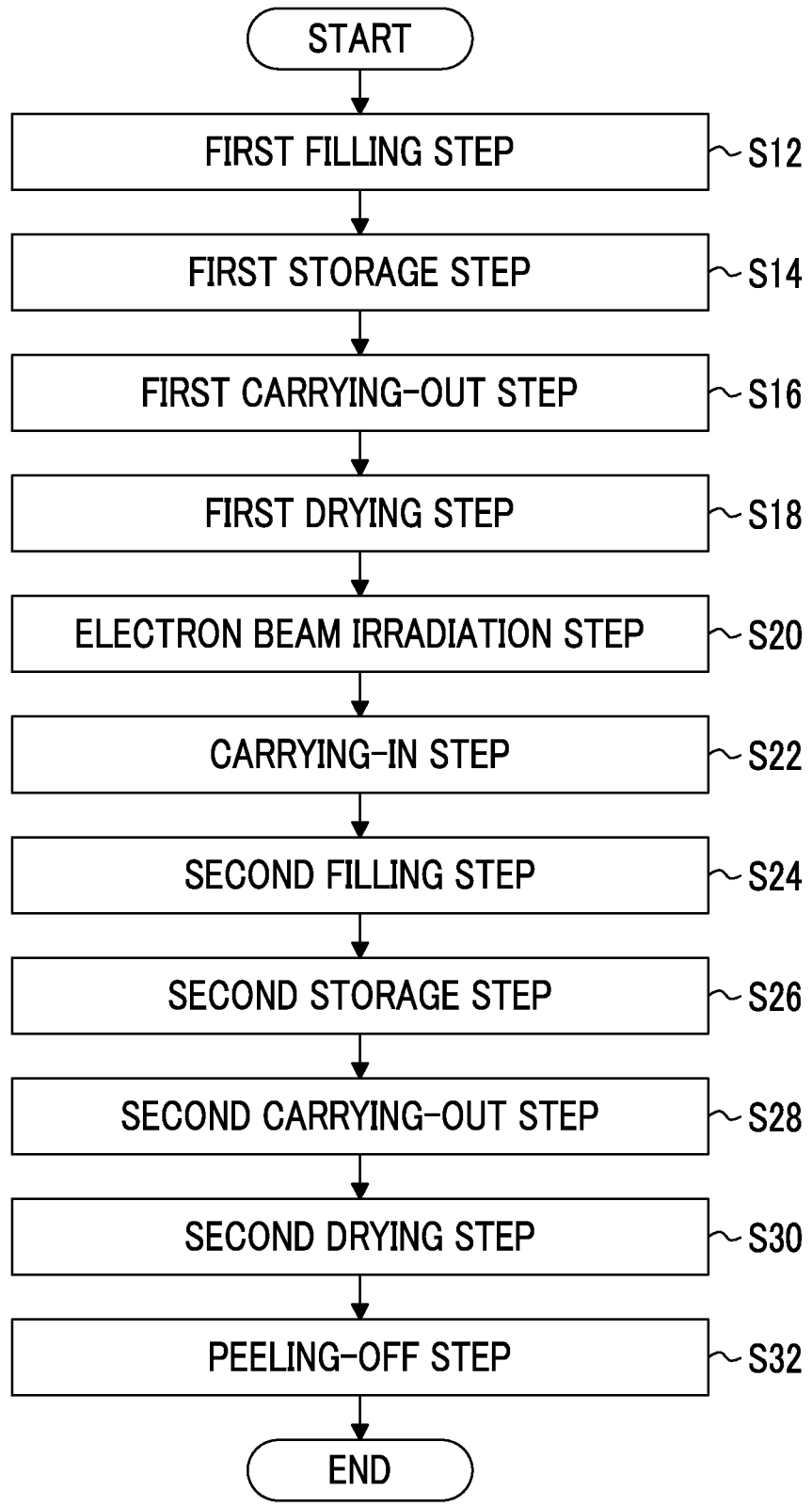
FIG. 5 is a flowchart of a method for manufacturing a transdermal absorption sheet.
Figure 6:
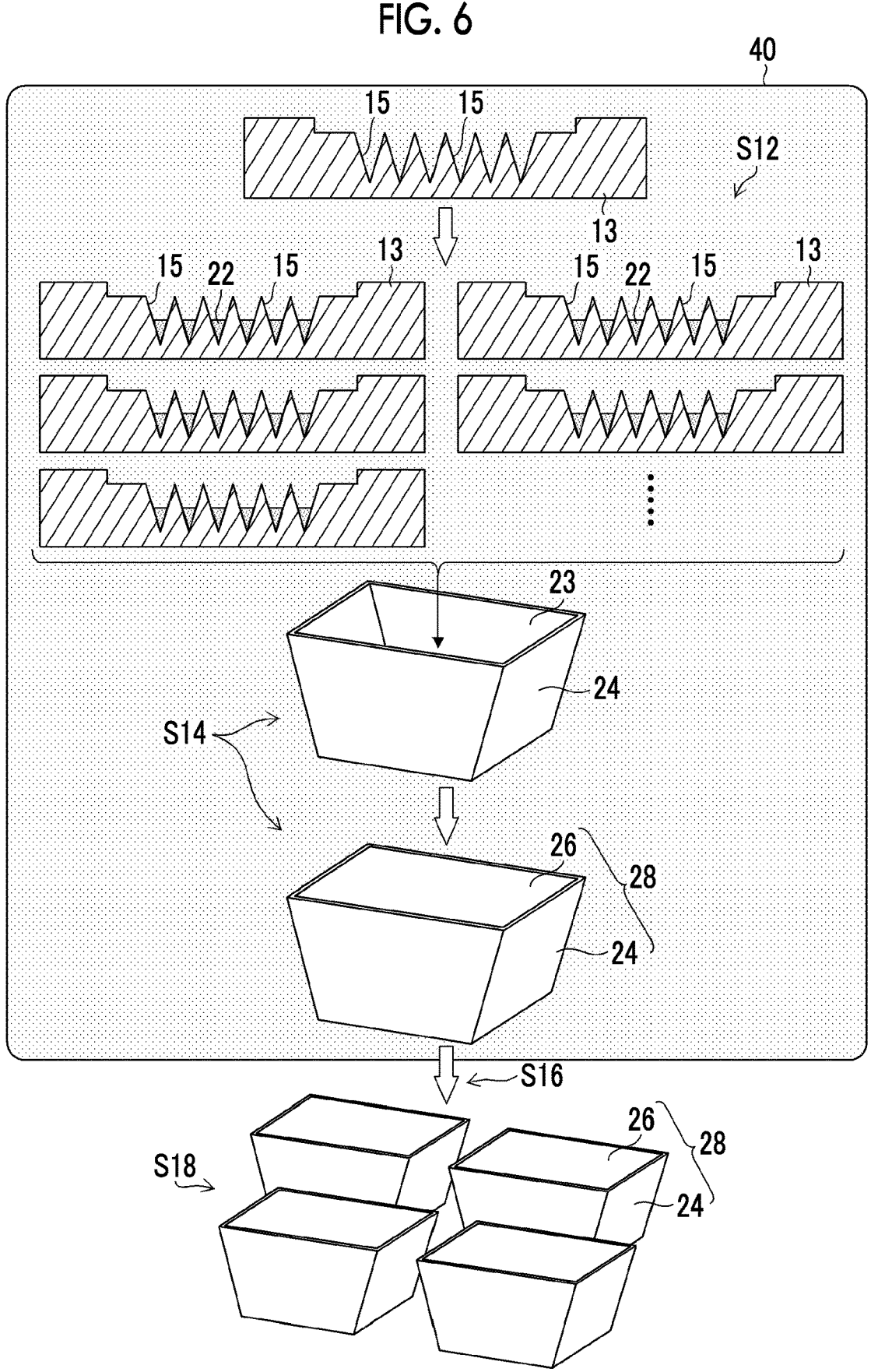
FIG. 6 is a diagram illustrating the method for manufacturing a transdermal absorption sheet.
Figure 7:
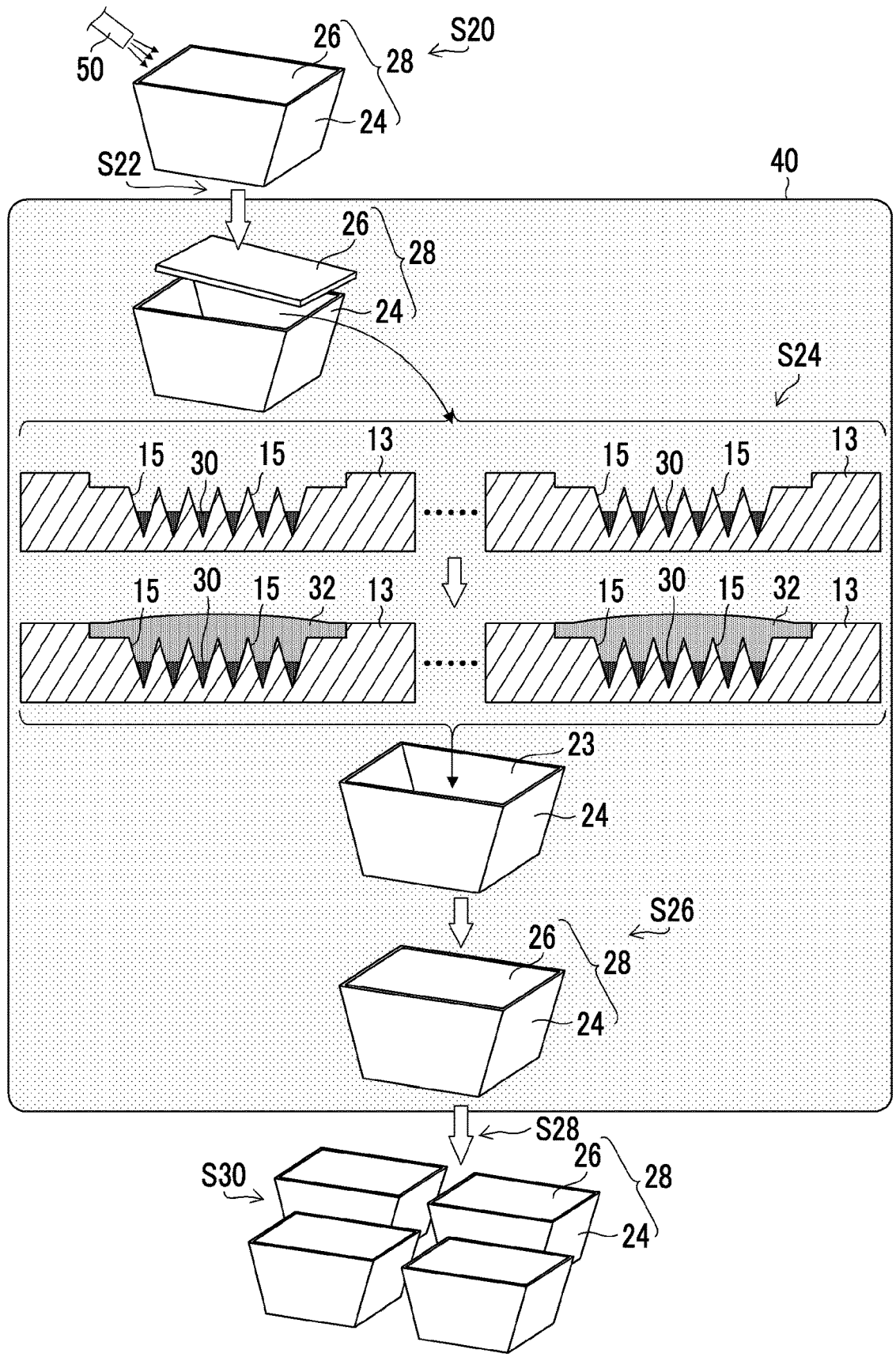
FIG. 7 is a diagram illustrating the method for manufacturing a transdermal absorption sheet.

FIG. 5 is a flowchart of a method for manufacturing a transdermal absorption sheet. FIGS. 6 and 7 are diagrams for illustrating the method for manufacturing a transdermal absorption sheet.

A method for manufacturing a transdermal absorption sheet according to an embodiment includes a first filling step (step S12) of filling needle-like recessed portions 15 of a mold 13 having the needle-like recessed portions 15 with a first polymer solution containing a drug in an aseptic environment, a first storage step (step S14) of storing the mold 13 filled with the first polymer solution in a drying container in an aseptic environment, a first carrying-out step (step S16) of carrying the drying container in which the mold 13 is stored out of the aseptic environment, a first drying step (step S18) of drying the first polymer solution of the mold 13 stored in the drying container outside an aseptic environment, an electron beam irradiation step (step S20) of irradiating a surface of the drying container in which the mold 13 is stored with an electron beam from an electron beam source, a carrying-in step (step S22) of carrying the drying container into an aseptic environment, a second filling step (step S24) of filling the needle-like recessed portions 15 of the mold 13 with a second polymer solution, a second storage step (step S26) of storing the mold 13 filled with the second polymer solution in a drying container in an aseptic environment, a second carrying-out step (step S28) of carrying the drying container in which the mold 13 is stored out of the aseptic environment, a second drying step (step S30) of drying the second polymer solution of the mold 13 stored in the drying container outside an aseptic environment, and a peeling-off step (step S32) of peeling off a transdermal absorption sheet manufactured by drying the second polymer solution from the mold 13. In addition, in the electron beam irradiation step, a shield that shields the electron beam is arranged at a position on a straight line connecting the electron beam source (electron beam irradiation point) and the needle-like recessed portions 15.

[First Filling Step: Step S12]

The first filling step is a step of filling the needle-like recessed portions 15 of the mold 13 with a first polymer solution 22 containing a drug in an aseptic environment.

As shown in FIG. 6, first, the mold 13 having needle-like recessed portions is prepared inside an aseptic room 40 in an aseptic environment. As the aseptic room 40, for example, an isolator and the like may be used. The mold 13 is subjected to a sterilization treatment (aseptic treatment) in advance to kill bacteria attached to the mold 13. Examples of the sterilization treatment include autoclave and electron beam irradiation.

The needle-like recessed portion 15 of the mold 13 are filled with the first polymer solution 22 containing a drug. As the filling method, the distal end portion of a slit nozzle may be brought into contact with the mold 13 to fill only the needle-like recessed portions 15. The needle-like recessed portions 15 may be filled with the first polymer solution 22 by applying the first polymer solution 22 onto the mold 13 with a nozzle, a dispenser or the like, and bringing the blade into contact with the mold 13.

[First Storage Step: Step S14]

The first storage step is a step of storing the mold 13 in which the needle-like recessed portions 15 are filled with the first polymer solution 22 in a drying container 28 in an aseptic environment.

The drying container 28 is subjected to a sterilization treatment in advance similar to the mold 13. As shown in FIG. 6, the drying container 28 includes a container body 24 and a lid 26. The container body 24 and the lid 26 are formed of a resin or a metal, respectively, and has microbial impermeability. The container body 24 has an opening portion 23 at the top portion.

The mold 13 after the first filling step is stored in the container body 24 through the opening portion 23. A plurality of molds 13 can be stored in the container body 24. Thereafter, the opening portion 23 is closed by the lid 26, and the space inside the drying container 28 is sealed. In order to surely close the container, the container body 24 and the lid 26 are preferably connected by welding or the like. As long as the container can be closed so that foreign matter and bacteria do not enter the container, the container body and the lid may be connected with a screw or a bolt. Since the first storage step is performed inside the aseptic room 40, the inside of the drying container 28 can be kept in an aseptic environment.

[First Carrying-Out Step: Step S16]

The first carrying-out step is a step of carrying the drying container 28 in which the mold 13 is stored out of the aseptic room 40 (out of the aseptic environment). Since the mold 13 is stored inside the drying container 28 that is sealed in the first storage step, even in a case where the drying container 28 is carried out of the aseptic room 40, the first polymer solution 22 inside the drying container 28 is not contaminated by bacteria and foreign matter.

[First Drying Step: Step S18]

The first drying step is a step of drying the first polymer solution 22 in the needle-like recessed portions 15 of the mold 13 stored in the drying container 28 outside an aseptic environment.

The first drying step is preferably performed in a drying box where the temperature and humidity can be adjusted. In a case where the drying speed of the first polymer solution 22 becomes faster, the shrinkage due to the drying rapidly progresses, it is difficult to form needle-like protruding portions 10 (refer to FIG. 1) along the shape of the needle-like recessed portions 15, and thus it is necessary to dry the first polymer solution slowly.

Although it takes about 3 hours to dry the first polymer solution 22, according to the embodiment, by performing the first drying step outside the aseptic room 40, the first filling step can be performed using the next mold 13 inside the aseptic room 40. Therefore, the next transdermal absorption sheet 1 can be manufactured without waiting for the completion of the first drying step, and the productivity can be improved.

[Electron Beam Irradiation Step: Step S20]

After the first polymer solution 22 is dried by the first drying step, the drying container 28 is returned to the inside of the aseptic room 40. The electron beam irradiation step is a step of, before carrying the drying container 28 in which the mold 13 is stored into the aseptic room 40, irradiating the surface of the drying container 28 with an electron beam from an electron beam source 50 to sterilize the surface of the drying container 28. In the electron beam irradiation step, a shield that shields the electron beam is arranged at a position on the straight line connecting the electron beam source 50 and the needle-like recessed portions 15.

Figure 8:
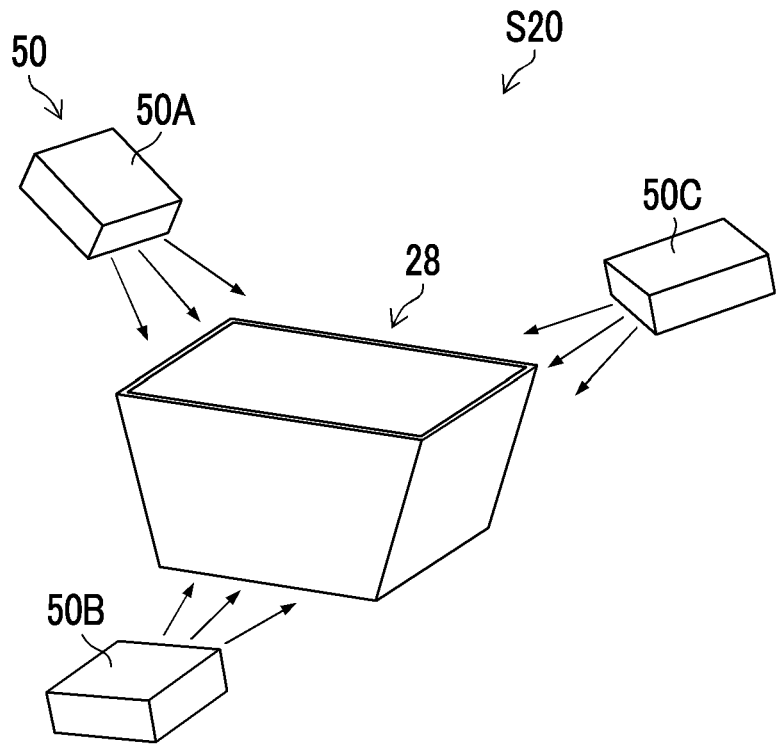
FIG. 8 is a diagram showing an arrangement of an electron beam source and a drying container.

FIG. 8 is a diagram showing an example of an arrangement of the electron beam source 50 and the drying container 28 in the electron beam irradiation step. Here, the surface of the drying container 28 is irradiated with the electron beam from three electron beam sources 50A, 50B, and 50C that are arranged in three equiangular directions with respect to the drying container 28. The method of supporting the drying container 28 is not particularly limited as long as the surface of the drying container 28 can be irradiated with the electron beam. Since the electron beam is easily scattered, the irradiation direction of the electron beam does not matter, and the surface of the drying container 28 can be sterilized by the arrangement shown in FIG. 8. For sterilization, the surface of the drying container 28 is preferably irradiated with an electron beam at an electron dose of 15 kilo grays (kGy) or more, and in the embodiment, the surface of the drying container 28 is irradiated with an electron beam at an electron dose of 15 kGy.

Figure 9:
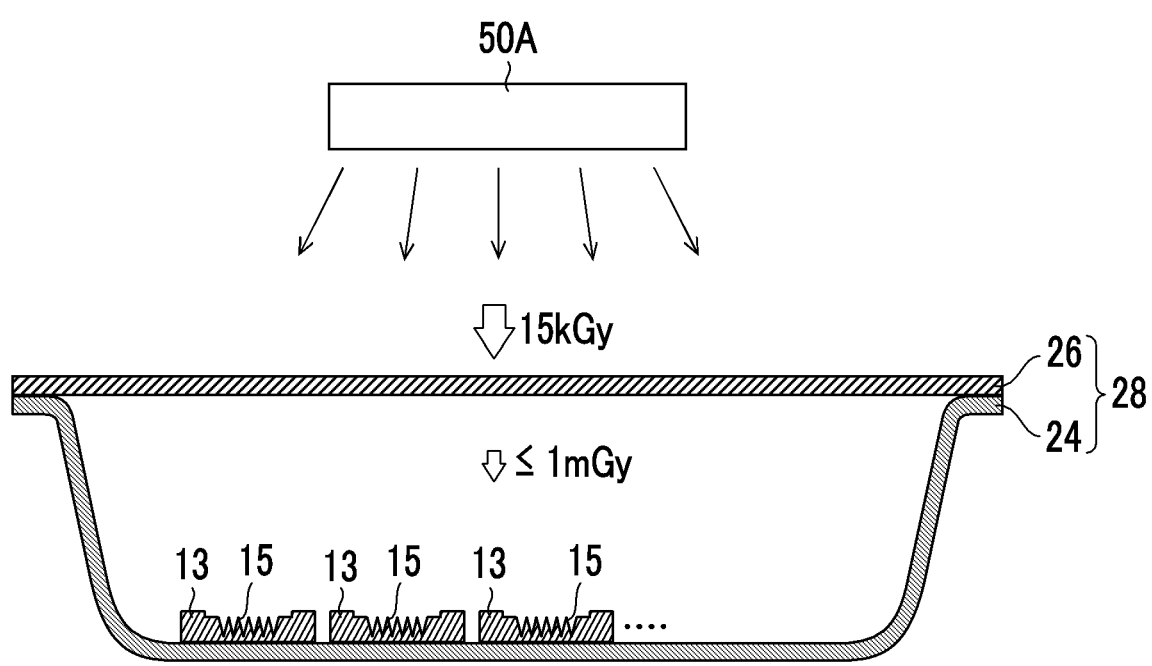
FIG. 9 is a schematic view showing an electron beam applied in an electron beam irradiation step.

FIG. 9 is a schematic view showing an electron beam applied in the electron beam irradiation step. As shown in FIG. 9, an electron beam is emitted from the electron beam source 50A, and the lid 26 is irradiated with the electron beam at an electron dose of 15 kGy. As a result, the lid 26 is sterilized. In addition, since the lid 26 is formed of a resin or a metal, the lid shields the electron beam. Therefore, the electron dose emitted from the electron beam source 50A and applied to the inside of the needle-like recessed portions 15 is 1 milli gray (mGy) or less. That is, the lid 26 functions as a shield arranged at a position on a straight line connecting the electron beam source 50A and the needle-like recessed portions 15. Thus, an adverse effect caused by irradiation of the dried first polymer solution 22 (intermediate, pharmaceutical preparation) inside the needle-like recessed portions 15 and the drug (raw material) contained in the first polymer solution 22 with the electron beam can be suppressed.

Although not shown in FIG. 9, electron beams are emitted from the electron beam sources 50B and 50C, respectively, and the container body 24 is irradiated with the electron beams at an electron dose of 15 kGy. As a result, the container body 24 is sterilized. In addition, since the container body 24 is also formed of a resin or a metal, the container shields the electron beams. Therefore, the electron dose emitted from the electron beam sources 50B and 50C and applied to the inside of the needle-like recessed portions 15 is 1 mGy or less. That is, the container body 24 functions as a shield arranged at a position on a straight line connecting the electron beam sources 50B and 50C and the needle-like recessed portions 15. Thus, an influence of the electron beams on the first polymer solution 22 inside the needle-like recessed portions 15 and the drug contained in the first polymer solution 22 can be suppressed.

Although a plurality of electron beam sources 50A, 50B, and 50C are used here, the container body may be irradiated with an electron beam from a plurality of directions of the drying container 28 by moving one electron beam source 50 around the drying container 28, or may be irradiated with an electron beam from a plurality of directions of the drying container 28 by changing the direction of the drying container 28 with respect to one electron beam source 50 which emits an electron beam in one direction.

As described above, in the embodiment, the shield arranged at the position on the straight line connecting the electron beam source 50 and the needle-like recessed portions 15 is the drying container 28. Therefore, it is possible to suppress the influence of the electron beam on the dried first polymer solution 22 inside the needle-like recessed portions 15 and the drug contained in the first polymer solution 22.

[Carrying-in Step: Step S22]

The carrying-in step is a step of carrying the sterilized drying container 28 into an aseptic environment after the electron beam irradiation step. As shown in FIG. 7, the drying container 28 is carried into the aseptic room 40. Since the surface of the drying container 28 is sterilized by the electron beam irradiation step, even in a case where the drying container 28 is returned to the inside of the aseptic room 40, the aseptic environment inside the aseptic room 40 can be maintained.

[Second Filling Step: Step S24]

The lid 26 is removed from the container body 24 of the drying container 28 carried into the aseptic room 40, and the mold 13 stored in the container body 24 is taken out from the opening portion 23. The opened drying container 28 may be discarded or, in a case where the drying container can be reused, the drying container may be reused.

In the needle-like recessed portions 15 of the mold 13, a drug-containing layer 30, which is a layer obtained by drying the first polymer solution 22, is formed.

The second filling step is a step of filling the needle-like recessed portions 15 of the mold 13 with a second polymer solution 32 (base liquid). As the filling method, a method of applying the second polymer solution with a dispenser can be used. In addition, in addition to coating with a dispenser, bar coating, spin coating, coating using a spray or the like can be applied.

[Second Storage Step: Step S26]

The second storage step is a step of storing the mold 13 filled with the second polymer solution 32 in the drying container 28 in an aseptic environment. Similar to the first storage step, the mold 13 after the second filling step is stored in the container body 24 through the opening portion 23 and the opening portion 23 is closed by the lid 26. Thus, the inside of the drying container 28 is kept in an aseptic environment.

[Second Carrying-Out Step: Step S28]

The second carrying-out step is a step of carrying the drying container 28 in which the mold 13 is stored out of the aseptic room 40 (out of the aseptic environment). Since the mold 13 is stored inside the drying container 28 that is sealed in the second storage step, even in a case where the drying container 28 is carried out of the aseptic room 40, the second polymer solution 32 inside the drying container 28 or the like is not contaminated with bacteria and foreign matter.

[Second Drying Step: Step S30]

The second drying step is a step of drying the second polymer solution 32 in the needle-like recessed portions 15 of the mold 13 stored in the drying container 28 outside an aseptic environment. The second drying step can be performed by the same method as the first drying step.

Although it takes 7 to 8 hours to dry the second polymer solution 32, the first filling step or the second filling step can be performed inside the aseptic room 40 by performing the second drying step outside the aseptic room 40. Therefore, the next transdermal absorption sheet 1 can be manufactured without waiting for the completion of the second drying step, and the productivity can be improved.

Figure 10:
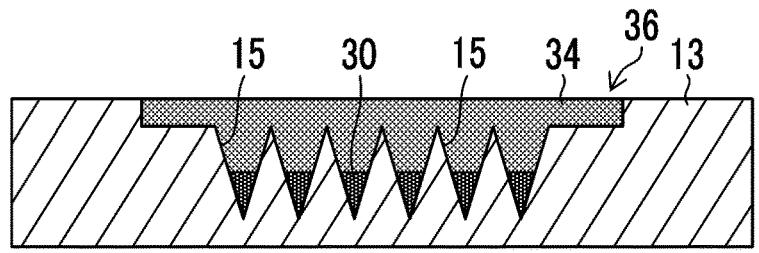
FIG. 10 is a diagram showing the mold after the completion of a second drying step.

FIG. 10 is a diagram showing the mold 13 after the completion of the second drying step. As shown in FIG. 10, by the second drying step, a transdermal absorption sheet 36 including the drug-containing layer 30 and a non-drug-containing layer 34 is formed in the mold 13.

As described above, the aseptic room 40 may have a space for performing the filling step (first filling step and second filling step) and the storage step (first storage step and second storage step), and a space for performing the drying step (first drying step and second drying step) is not required. Therefore, the aseptic environment area such as the aseptic room 40 can be narrowed in the manufacturing equipment, and the cost of manufacturing equipment can be reduced.

[Peeling-Off Step: Step S32]

The lid 26 is removed from the container body 24 of the drying container 28, and the stored mold 13 is taken out from the opening portion 23.

The peeling-off step is a step of peeling off the transdermal absorption sheet 36 from the mold 13. A peeling method is not particularly limited. It is desirable that the drug-containing layer 30 and the non-drug-containing layer 34 are not bent or broken during peeling-off.

Figure 11:
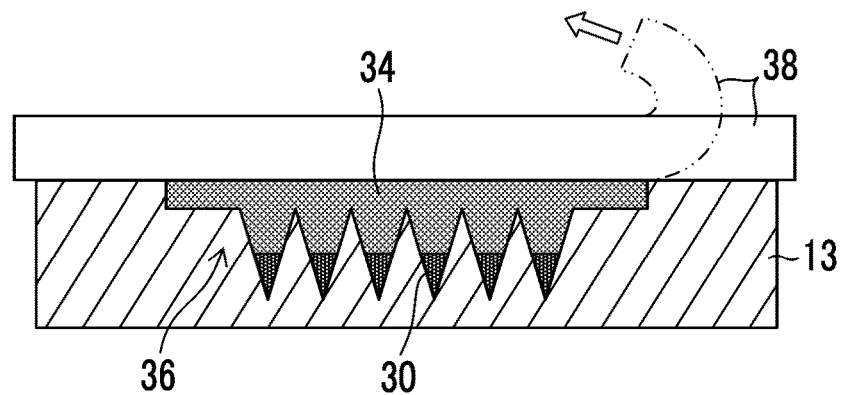
FIG. 11 is a diagram for illustrating a peeling-off step.
Figure 12:
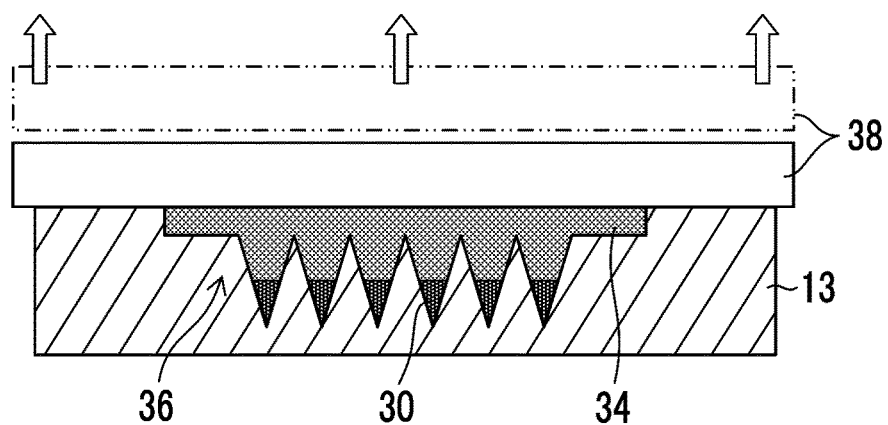
FIG. 12 is a diagram for illustrating the peeling-off step.

FIGS. 11 and 12 are diagrams for illustrating the peeling-off step. As shown in FIG. 11, after a sheet-like substrate 38 on which a pressure sensitive adhesive layer having pressure sensitive adhesiveness is formed is attached to a rear surface (a surface on a side close to the non-drug-containing layer 34) of the transdermal absorption sheet 36, peeling-off can be performed so that the substrate 38 is turned over from the end portion. However, in this method, there is a possibility that the drug-containing layer 30 and the non-drug-containing layer 34 may be bent. Therefore, as shown in FIG. 12, a method can be applied in which the substrate 38 is placed on the transdermal absorption sheet 36 with a sucker (not shown), and the substrate is vertically lifted while being sucked with air.

Figure 13:
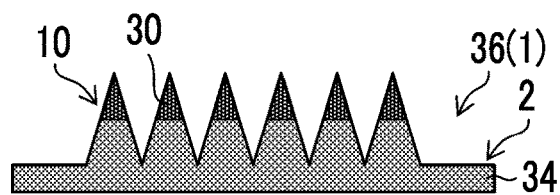
FIG. 13 is a diagram showing a transdermal absorption sheet peeled off from the mold.

FIG. 13 is a diagram showing the transdermal absorption sheet 36 peeled off from the mold 13. The transdermal absorption sheet 36 includes the drug-containing layer 30 and the substantially non-drug-containing layer 34. The transdermal absorption sheet 36 corresponds to the transdermal absorption sheet 1 shown in FIG. 1, the sheet portion 2 is constituted by a part of the non-drug-containing layer 34, and the needle-like protruding portion 10 is constituted by a part of the drug-containing layer 30 and a part of the non-drug-containing layer 34.

In a case where the structure of the needle-like protruding portions having a high aspect ratio is peeled off from the mold 13 as in the embodiment, the contact area is large and thus a strong stress is applied. There is concern that the needle-like protruding portions 10 may be destroyed and remain in the needle-like recessed portions 15 without being peeled off from the mold 13, and the transdermal absorption sheet to be produced may have a defect. In the embodiment, it is preferable that the material forming the mold 13 is formed of an easily peelable material. In addition, by using a material high elasticity and softness as the material forming the mold 13, the stress applied to the needle-like protruding portions 10 at peeling-off can be relaxed.

Here, the peeling-off step is performed outside the aseptic room 40. However, in a case where the peeling-off step is performed inside the aseptic room 40, the drying container 28 is carried into the aseptic room 40 after the electron beam irradiation step is performed.

Second Embodiment

In the first embodiment, the mold 13 is handled as it is, but a transporting holding device for mounting the mold 13 may be used.

Figure 14:
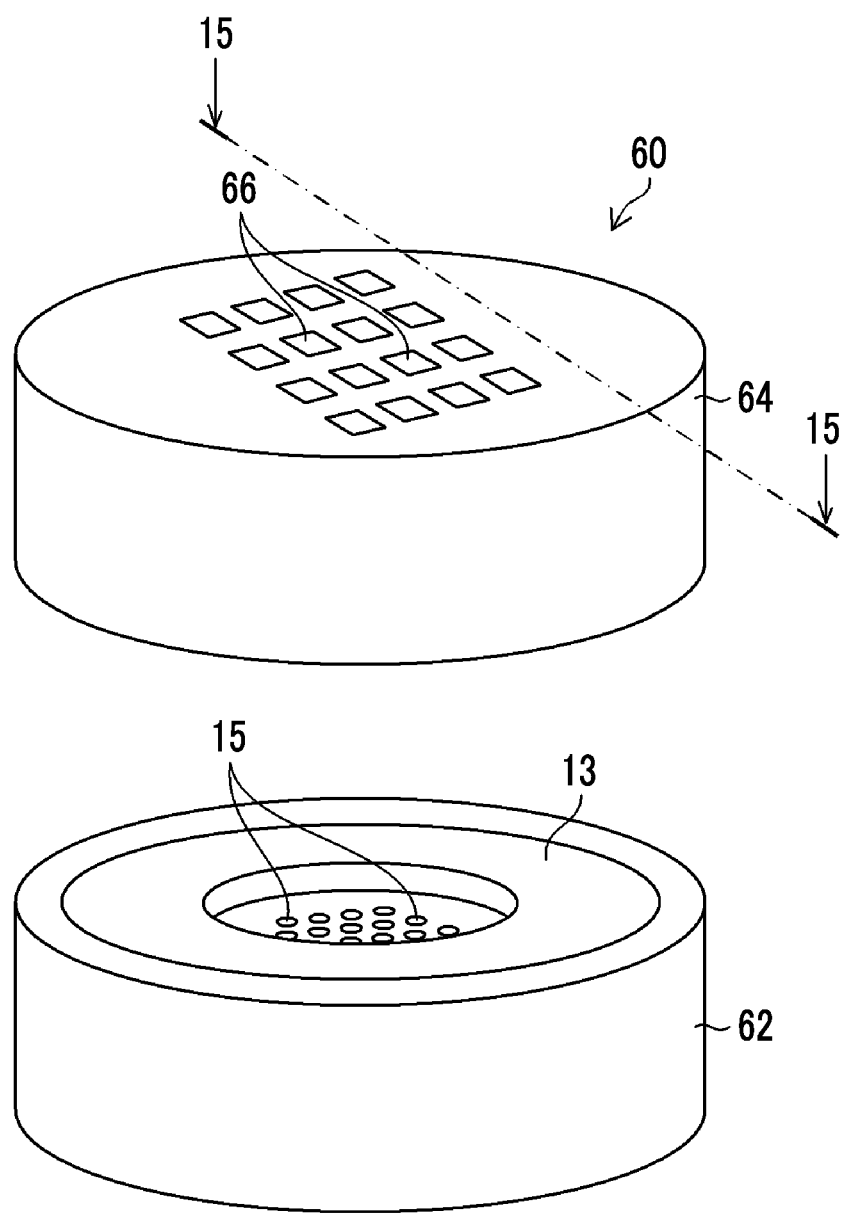
FIG. 14 is a perspective view of a transporting holding device.
Figure 15:
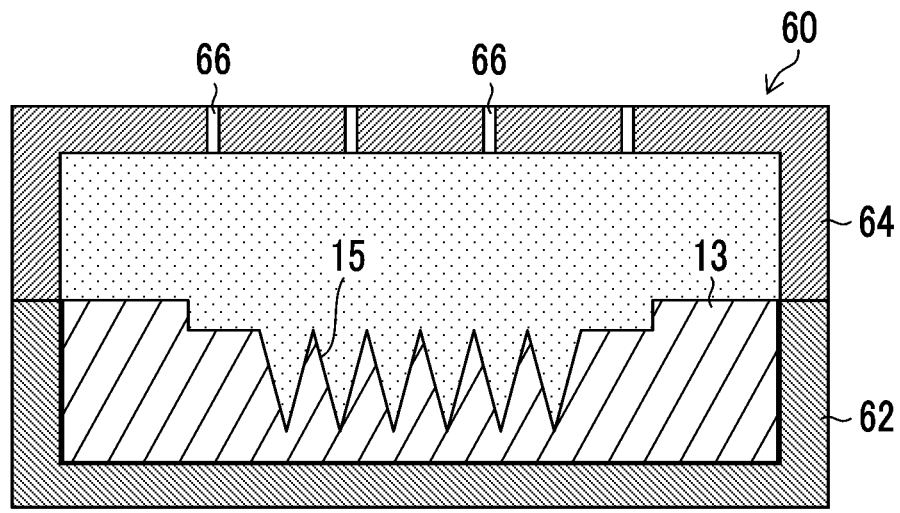
FIG. 15 is a cross-sectional view taken along line 15-15 of FIG. 14.

FIG. 14 is a perspective view of a transporting holding device 60. FIG. 15 is a cross-sectional view taken along line 15-15 of FIG. 14. The transporting holding device 60 includes a pedestal portion 62 and a cap portion 64. The pedestal portion 62 and the cap portion 64 are each formed of a resin or a metal.

The mold 13 is placed on the pedestal portion 62. The first filling step (step S12) and the second filling step (step S24) can be performed in a state in which the mold 13 is placed on the pedestal portion 62.

The cap portion 64 is attached to the pedestal portion 62 and covers the upper surface of the needle-like recessed portions 15 of the mold 13. The cap portion 64 is attached to the pedestal portion (cover step) after the first filling step (step S12) and before the first storage step (step S14) and after the second filling step (step S24) and before the second storage step (step S26). The mold 13 is stored in the drying container 28 in the first storage step (step S14) and the second storage step (step S26) in a state in which the cap portion 64 of the transporting holding device 60 is attached.

The top surface of the cap portion 64 is provided with a plurality of through-holes 66 (an example of a communication passage) extending in the vertical direction. The through-holes 66 serve as escape paths for water vapor during drying. By appropriately providing the size, the number, the arrangement, and the like of the through-holes 66 that communicate with the cap portion 64, the drying time of the first polymer solution 22 in the first drying step (step S18) and the drying time of the second polymer solution 32 in the second drying step (step S30) can be adjusted to be appropriate.

The transporting holding device 60 functions as an electron beam shield. Even in a case where the electron dose of 15 kGy is applied to the side surface and the lower surface of the transporting holding device 60, the electron dose applied from the inside of the needle-like recessed portions 15 of the mounted mold 13 is 1 mGy or less.

Figure 16:
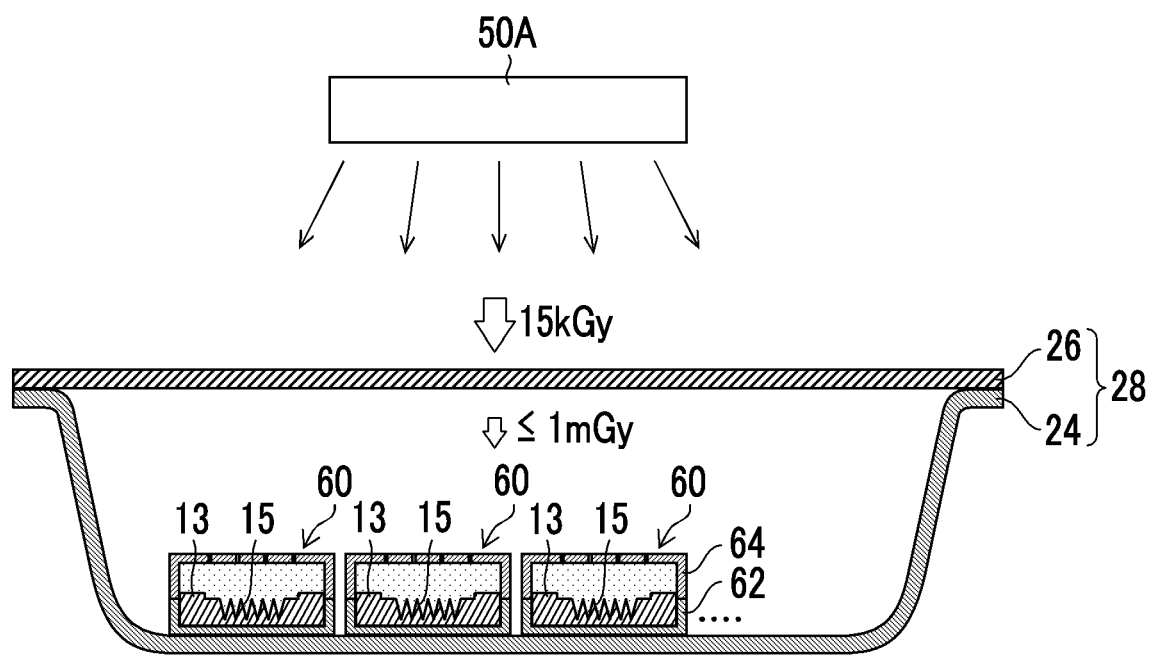
FIG. 16 is a schematic view showing an electron beam applied in the electron beam irradiation step.

FIG. 16 is a schematic view showing an electron beam applied in the electron beam irradiation step in a case of using the transporting holding device 60. As shown in FIG. 16, in the drying container 28, a plurality of molds 13 mounted on the transporting holding device 60 are stored.

As shown in FIG. 16, an electron beam is emitted from the electron beam source 50A, and the lid 26 is irradiated with an electron beam at an electron dose of 15 kGy. The electron beam is shielded by the lid 26. Therefore, the electron dose emitted from the electron beam source 50A and applied to the inside of the needle-like recessed portions 15 is 1 mGy or less.

Third Embodiment

At least a part of the drying container 28 may be formed of a material having microbial impermeability and gas permeability. By forming a part of the drying container with a material having gas permeability, the first polymer solution 22 and the second polymer solution 32 can be appropriately dried. In addition, the drying speed can be controlled by controlling the pressure inside the dry cabinet.

Further, by forming a part of the drying container with a material having microbial impermeability, it is possible to prevent foreign matter and bacteria from entering the container from the outside of the drying container 28. Therefore, even in a case where the drying container 28 is placed (exposed) outside an aseptic environment, the inside the drying container 28 can be kept in an aseptic environment.

The "microbial impermeability" is sufficient as long as the level of microbial impermeability is a level of impermeability of microorganisms of commercially available sterilization packaging materials (a bag for sterilization or the like). Therefore, the microbial impermeability level may be appropriately selected from commercially available sterilization packaging materials according to the purpose. More specifically, a material having LRV≥3.0 is preferable for microbial impermeability. LRV can be calculated by the following expression.

$$LRV = \log_{10}(A/B)$$

A: Number of microorganisms per ml before passing through the material

B: Number of microorganisms per ml after passing through the material

Since the higher the LRV, the smaller the number of permeation of microorganisms, the upper limit of LRV is not particularly limited, but the upper limit is preferably LRV≤9. In order to secure such microbial impermeability, a material having a pore size of 0.2 μm is generally used. As the material having microbial impermeability, both materials used for microorganisms in a gas and materials used for microorganisms in a liquid can be used.

The level of gas permeability can also be appropriately selected according to the purpose. Since the drying container has the gas permeability, the gas generated by the drying inside the drying container 28 can escape to the outside of the drying container 28, and the drying can be promoted. For the gas permeability, for example, a material having a water vapor permeability of 1500 to 1640 g/m$^2$/24 hours measured at 23° C. and a relative humidity of 85% according to TAPPI T523 is preferable, and a material having a water vapor permeability of 1615 g/m$^2$/24 hours is more preferable.

As such a material having microbial impermeability and gas permeability, a porous sheet can be used, and specifically, a high density polyethylene nonwoven fabric sheet can be used. The high density polyethylene nonwoven fabric sheet is a sheet in which ultrafine long polyethylene fibers having a fiber diameter of 0.5 to 10 μm are randomly laminated and bonded only by heat and pressure, and for example, TYVEK (registered trademark) sheet manufactured by DuPont may be used.

Figure 17:
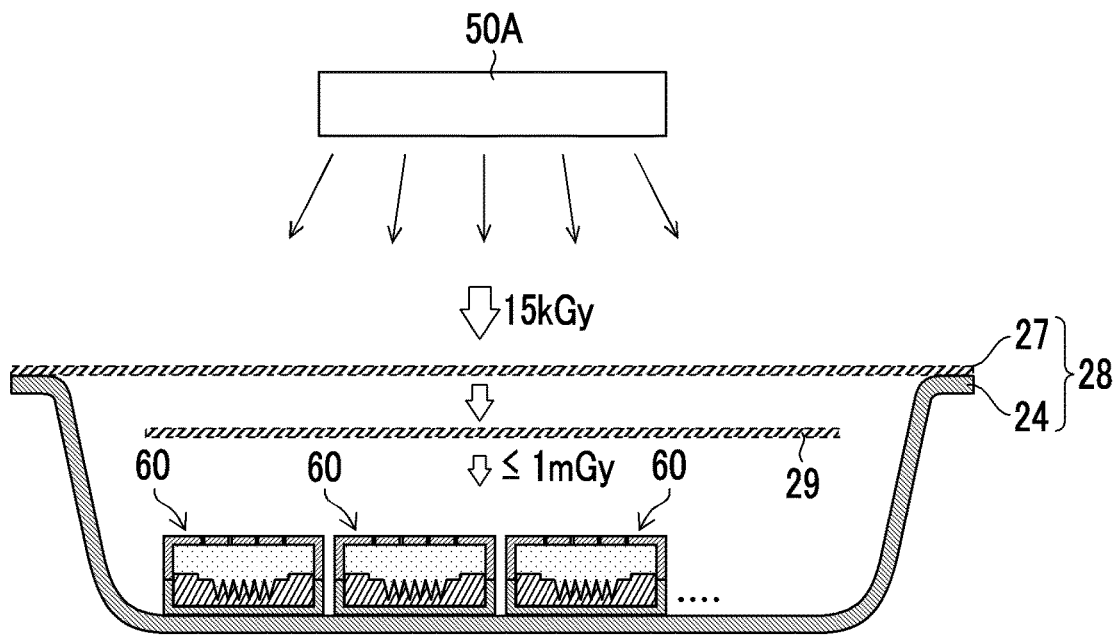
FIG. 17 is a schematic view showing an electron beam applied in the electron beam irradiation step.

FIG. 17 is a schematic view showing an electron beam applied in the electron beam irradiation step. In the drying container 28 shown in FIG. 17, the container body 24 (electron beam shielding portion) is formed of a resin or a metal as before, and the lid 27 (gas permeation portion) is constituted of a porous sheet. The lid 27 of the porous sheet allows the evaporation of water from the needle-like recessed portions 15 of the mold 13 to escape to the outside of the drying container 28.

As shown in FIG. 17, in the drying container 28, a plurality of molds 13 mounted on the transporting holding device 60 are stored. Further, one porous sheet 29 is provided between the lid 27 and the transporting holding device 60.

As shown in FIG. 17, an electron beam is emitted from the electron beam source 50A, and the lid 27 is irradiated with an electron beam at an electron dose of 15 kGy. As a result, the lid 27 is sterilized. Since the lid 27 is formed of a porous sheet, the electron beam shielding rate is relatively low, and the electron beam cannot be sufficiently shielded. In a case where there is no shield that shields the electron beam, the electron beam having passed through the lid 27 passes through the through-holes 66 extending in the vertical direction and is applied to the needle-like recessed portions 15 of the mold 13. Therefore, here, the porous sheet 29 is arranged as a shield at a position on the straight line connecting the lid 27 and the needle-like recessed portions 15.

Although the electron beam cannot be sufficiently shielded only by the porous sheet of the lid 27, by further arranging the porous sheet 29 to form a two-porous sheet constitution, the electron dose applied to the inside of the needle-like recessed portions 15 is set to 1 mGy or less. As a result, the influence of the electron beam on the dried first polymer solution 22 inside the needle-like recessed portions 15 and the drug contained in the first polymer solution 22 can be suppressed.

The porous sheet 29 may be placed on the mold 13 after the mold 13 is stored in the container body 24 through the opening portion 23 in the first storage step (step S14) and the second storage step (step S26). In a case where the transporting holding device 60 is used, the porous sheet may be placed on the transporting holding device 60. Thus, in the electron beam irradiation step, the electron beam passing through the lid 27 arranged on the upper surface of the drying container 28 can be shielded by the porous sheet 29 placed on the needle-like recessed portions 15.

Although the porous sheet 29 is arranged as the shield here, any plate or sheet formed of a resin or a metal may be used as long as the plate or sheet can shield the electron beam. From the viewpoint of appropriately drying the first polymer solution 22 and the second polymer solution 32, a porous material that does not disturb evaporation of water is preferable, and a porous material having high gas permeability is more preferable.

Since the lid 27 side is not directly irradiated with the electron beam, the electron beam can be prevented from passing through the through-holes 66 of the transporting holding device 60 and irradiating the needle-like recessed portions 15 of the mold 13.

Fourth Embodiment

Figure 18:
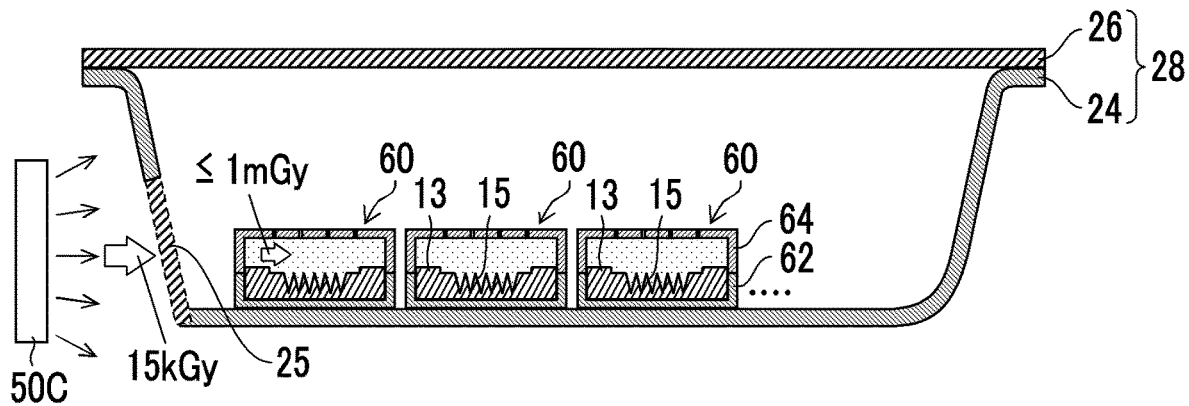
FIG. 18 is a schematic view showing an electron beam applied in the electron beam irradiation step.

In the drying container 28, the container body 24 may be formed of a material having microbial impermeability and gas permeability. FIG. 18 is a schematic view showing an electron beam applied in the electron beam irradiation step. The drying container 28 shown in FIG. 18 has a container body 24 provided with a filter portion 25. The filter portion 25 (gas permeation portion) is constituted of a porous sheet, and the other container body 24 (electron beam shielding portion) is formed of a resin or a metal as before. In the drying container 28, a plurality of molds 13 mounted on the transporting holding device 60 are stored.

As shown in FIG. 18, an electron beam is emitted from the electron beam source 50C, and an electron dose of 15 kGy is applied to the container body 24 including the filter portion 25. As a result, the container body 24 including the filter portion 25 is sterilized. It should be noted that the filter portion 25 has a low electron beam shielding rate and cannot sufficiently shield the electron beam. Therefore, the electron beam having passed through the filter portion 25 is applied to the transporting holding device 60.

Here, the transporting holding device 60 is formed of a resin or a metal. Further, since the through-holes 66 extend in the vertical direction, the through-holes are not parallel to the straight line connecting the electron beam source 50 and the needle-like recessed portions 15, and the electron beam from the electron beam source 50C does not pass through the through-holes 66. Therefore, the electron beam passed through the filter portion 25 and applied to the transporting holding device 60 is shielded by the transporting holding device 60. Therefore, the electron dose applied from the electron beam source 50C to the inside of the needle-like recessed portions 15 is 1 mGy or less.

In this manner, the transporting holding device 60 functions as a shield that shields the electron beam at a position on the straight line connecting the electron beam source 50A and the needle-like recessed portions 15. Here, the transporting holding device 60 is arranged at a position on the straight line connecting the filter portion 25 (gas permeation portion) and the needle-like recessed portions 15.

A porous sheet may be arranged as a shield inside the container body 24 along the filter portion 25.

In addition, in the drying container 28, both the container body 24 and the lid 26 may be formed of a material having microbial impermeability and gas permeability. (gas permeation portion). As a result, the gas permeation region of the drying container 28 can be widened, and the drying speed can be increased. Also in this case, a shield that shields the electron beam may be arranged at a position on the straight line connecting the electron beam source 50 and the needle-like recessed portions 15.

Fifth Embodiment

Since the transporting holding device 60 shown in FIGS. 14 and 15 has a plurality of through-holes 66 extending in the vertical direction on the top surface of the cap portion 64, the transporting holding device 60 does not function as a shield against the electron beam applied from the upper surface. However, the following modification examples can be made.

Figure 19:
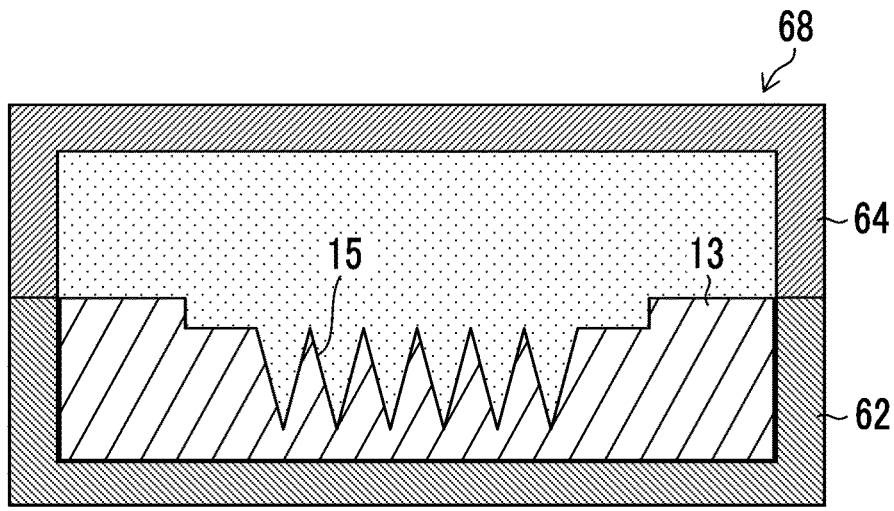
FIG. 19 is a diagram for illustrating the inside of a transporting holding device.

FIG. 19 is a diagram for illustrating the transporting holding device 68 and is a cross-sectional view similar to FIG. 15. The through-holes 66 are not provided in the cap portion 64 of the transporting holding device 68. Therefore, the cap portion 64 functions as a shield against the electron beam applied from the upper surface, and even in a case where the electron dose of 15 kGy is applied from the upper surface, the electron dose applied to the inside of the needle-like recessed portions 15 of the mounted mold 13 is 1 mGy or less. The same applies to the side surface and the lower surface. Therefore, even in a case where the drying container 28 (refer to FIG. 17) using the lid 27 consisting of a porous sheet is used, it is not necessary to use the porous sheet 29.

Figure 20:
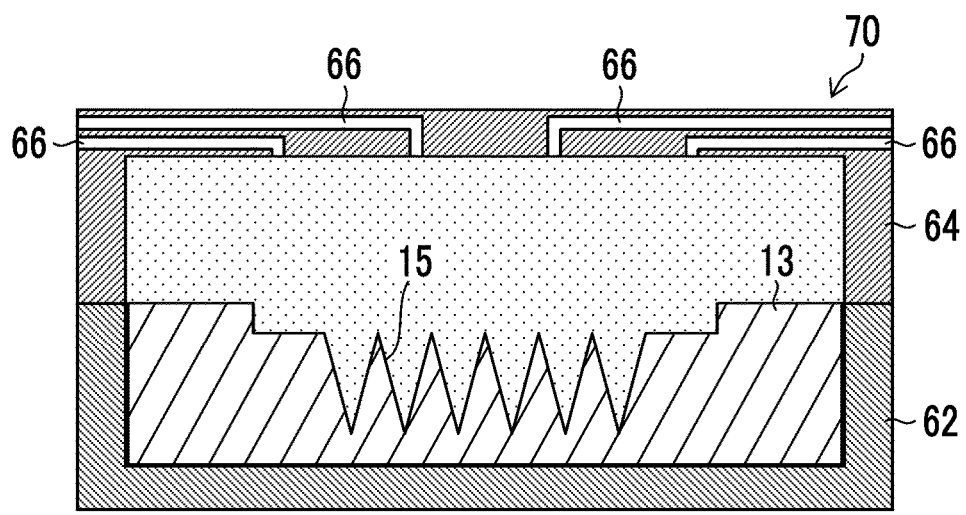
FIG. 20 is a diagram for illustrating the inside of a transporting holding device.

FIG. 20 is a diagram for illustrating the inside of a transporting holding device 70 and is a cross-sectional view similar to FIG. 15. The cap portion 64 of the transporting holding device 70 is provided with a plurality of through-holes 66 extending from the inside of the top surface of the cap portion 64 to the outside of the side surface. Therefore, the electron beam applied from the upper surface of the cap portion 64 can be shielded by the cap portion 64, and the electron beam does not directly enter the inside of the cap portion 64. In this manner, by arranging the through-holes 66 in a direction not parallel to the straight line connecting the electron beam source 50 and the needle-like recessed portions 15, the transporting holding device 70 can function as a shield.

Figure 21:
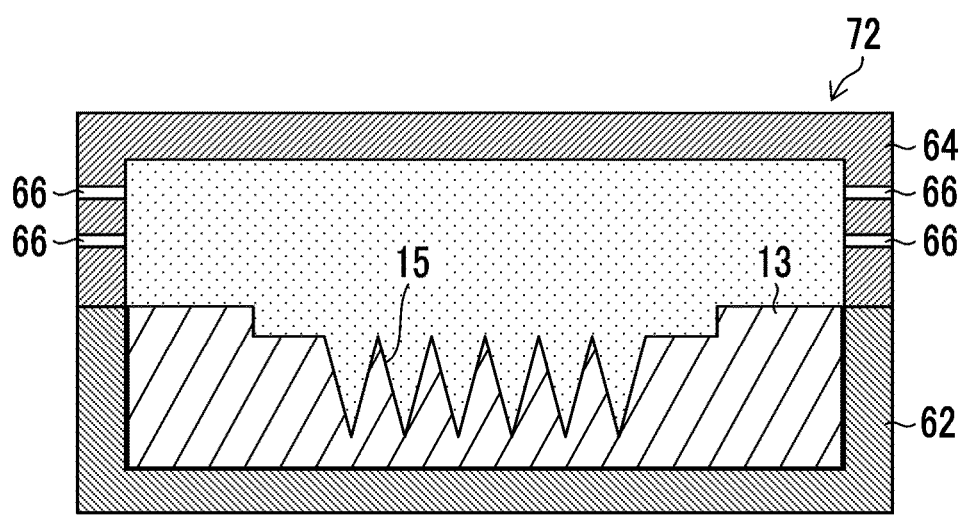
FIG. 21 is a diagram for illustrating the inside of a transporting holding device.

FIG. 21 is a diagram for illustrating the inside of a transporting holding device 72 and is a cross-sectional view similar to FIG. 15. The cap portion 64 of the transporting holding device 72 is provided with a plurality of through-holes 66 extending in the horizontal direction from the inside of the side surface of the cap portion 64 to the outside of the side surface. Therefore, the electron beam applied from the upper surface of the cap portion 64 can be shielded by the cap portion 64, and the electron beam does not directly enter the inside of the cap portion 64. In this manner, by arranging the through-holes 66 in a direction not parallel to the straight line connecting the electron beam source 50 and the needle-like recessed portions 15, the transporting holding device 72 can function as a shield.

<Others>

The technical scope of the present invention is not limited to the scope described in the above embodiment. The configuration and the like in each embodiment can be appropriately combined between the respective embodiments without departing from the gist of the present invention.

EXPLANATION OF REFERENCES

1: transdermal absorption sheet
2: sheet portion
10: needle-like protruding portion
11: original plate
12: shape portion
13: mold
15: needle-like recessed portion
22: first polymer solution
23: opening portion
24: container body
25: filter portion
26: lid
27: lid
28: drying container
29: porous sheet
30: layer
32: second polymer solution
34: layer
36: transdermal absorption sheet
38: substrate
40: aseptic room
50: electron beam source
50A: electron beam source
50B: electron beam source
50C: electron beam source
60: transporting holding device
62: pedestal portion
64: cap portion
66: through-hole
68: transporting holding device
70: transporting holding device
72: transporting holding device
S12 to S32: each step of method for manufacturing transdermal absorption sheet

What is claimed is:

1. A method for manufacturing a transdermal absorption sheet comprising:
   a first filling step of filling needle-shaped recessed portions of a mold having the needle-shaped recessed portions with a first polymer solution containing a drug or a cosmetic component in an aseptic environment;
   a storage step of storing the mold filled with the first polymer solution in a drying container in an aseptic environment;
   a carrying-out step of carrying the drying container in which the mold is stored out of the aseptic environment;
   a drying step of drying the first polymer solution of the mold stored in the drying container outside an aseptic environment;

an electron beam irradiation step of irradiating a surface of the drying container in which the mold is stored with an electron beam from an electron beam source; and a carrying-in step of carrying the drying container into an aseptic environment after the electron beam irradiation step, wherein in the electron beam irradiation step, a shield that shields an electron beam is arranged at a position on a straight line connecting the electron beam source and the needle-shaped recessed portions.

2. The method for manufacturing a transdermal absorption sheet according to claim 1, wherein the shield is the drying container.

3. The method for manufacturing a transdermal absorption sheet according to claim 1, wherein the drying container includes an electron beam shielding portion that shields an electron beam, and a gas permeation portion that has microbial impermeability and gas permeability and has a relatively lower electron beam shielding rate than the electron beam shielding portion, and the shield is arranged at a position on a straight line connecting the gas permeation portion and the needle-shaped recessed portions.

4. The method for manufacturing a transdermal absorption sheet according to claim 3, wherein the electron beam shielding portion is formed of a resin or a metal.

5. The method for manufacturing a transdermal absorption sheet according to claim 3, wherein the gas permeation portion is constituted of a porous sheet.

6. The method for manufacturing a transdermal absorption sheet according to claim 3, wherein the shield is a porous sheet.

7. The method for manufacturing a transdermal absorption sheet according to claim 3, wherein the gas permeation portion is arranged on an upper surface of the drying container, and the shield is placed between the gas permeation portion and the mold.

8. The method for manufacturing a transdermal absorption sheet according to claim 1, further comprising:

a cover step of covering the needle-shaped recessed portions of the mold filled with the first polymer solution with a holding device before the storage step, wherein the shield is the holding device.

9. The method for manufacturing a transdermal absorption sheet according to claim 8, wherein the holding device has a communication passage that allows an inside and an outside of the holding device to communicate with each other, and the communication passage is arranged not parallel to a straight line connecting the electron beam source and the needle-shaped recessed portions.

10. The method for manufacturing a transdermal absorption sheet according to claim 8, wherein the holding device is formed of a resin or a metal.

11. The method for manufacturing a transdermal absorption sheet according to claim 1, wherein in the electron beam irradiation step, an electron dose applied to the surface of the drying container is 15 kilo grays or more.

12. The method for manufacturing a transdermal absorption sheet according to claim 11, wherein in the electron beam irradiation step, an electron dose applied to the needle-shaped recessed portions is 1 mGy or less.

13. The method for manufacturing a transdermal absorption sheet according to claim 1, further comprising:

a second filling step of filling the needle-shaped recessed portions of the mold with a second polymer solution in an aseptic environment after the carrying-in step.

14. The method for manufacturing a transdermal absorption sheet according to claim 1, wherein the drug is peptide, protein, nucleic acid, polysaccharide, a vaccine, or a medical compound.

* * * * *